(12) United States Patent
Kramer et al.

(10) Patent No.: US 6,906,223 B2
(45) Date of Patent: Jun. 14, 2005

(54) METHOD FOR THE PRODUCTION OF TRIOXIME DERIVATIVES

(75) Inventors: Andreas Kramer, Bad Dürkheim (DE); Matthias Kiefer, Nussloch (DE); Michael Henningsen, Frankenthal (DE); Wolfgang Siegel, Limburgerhof (DE); Jochen Schröder, Lambsheim (DE)

(73) Assignee: BASF AG, Ludwigshafen (DE)

( * ) Notice: Subject to any disclaimer, the term of this patent is extended or adjusted under 35 U.S.C. 154(b) by 319 days.

(21) Appl. No.: 10/332,046
(22) PCT Filed: Jul. 4, 2001
(86) PCT No.: PCT/EP01/07660
§ 371 (c)(1), (2), (4) Date: Jan. 6, 2003
(87) PCT Pub. No.: WO02/02514
PCT Pub. Date: Jan. 10, 2002

(65) Prior Publication Data
US 2003/0163002 A1 Aug. 28, 2003

(30) Foreign Application Priority Data
Jul. 5, 2000 (DE) .......................................... 100 32 031

(51) Int. Cl.$^7$ ..................... C07C 249/08; C07C 251/60; C07C 49/12
(52) U.S. Cl. ...................... 564/259; 564/254; 564/255; 564/256; 564/262
(58) Field of Search ............................... 564/254–256, 564/259, 262

(56) References Cited

U.S. PATENT DOCUMENTS 5,948,932 A * 9/1999 Grote et al. ................ 558/422

FOREIGN PATENT DOCUMENTS

WO 00/18726 4/2000 ......... C07C/249/08

OTHER PUBLICATIONS

XP–002183768, Method. der Org. Chem., 4$^{th}$ ed. vol. ES, p 780–781 (1985).
Rev.Acad,Cuebc,Exatas,Bd.31,S.91–100 (1976) Alduan et al.
Bull.Acad.Sci.USSR.En,Bd.28,S.121–128 (1979) Mishchenko et al.
Ind.J.Chem.Bd,30B,S.749–753 (1991),Fadda.
XP–001022657, Gazz. Chim. Ital., vol. 22, p. 289–301 (1922).
Methoden der Org. Chem.Bd.10/4,77ff,55ff,217ff. (1979).
Gazz. Chim.Ital,Bd.22 S289ff.1922,Ponzio et al.

* cited by examiner

Primary Examiner—Brian Davis
(74) Attorney, Agent, or Firm—Novak Deuce & Quigg, LLP

(57) ABSTRACT

The present invention relates to a process for preparing trioxime derivatives of the formula I

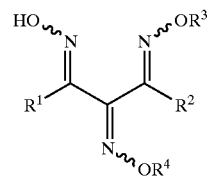

in which the substituents $R^1$ and $R^2$ are identical or different and each is cyano, alkyl, haloalkyl or cycloalkyl, and $R^3$ and $R^4$ are identical or different and each is alkyl, haloalkyl, cycloalkyl, alkylcarbonyl or arylalkyl, by the following reaction steps in water without isolation of the intermediates:

A) nitrosation of 1,3-diketones of the formula II

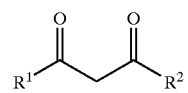

to give monooximes of the formula III,

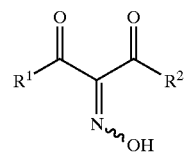

B) oximation of III with hydroxylamine derivatives of the formula IV $$H_2N—OR^{3'}$$  IV in which $R^{3'}$ is hydrogen or a group $R^3$ to give bisoximes of the formula V,

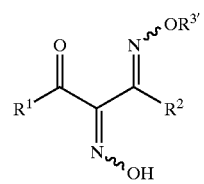

C) alkylation of V with alkylating agents or acylation of V with acylating agents to give compounds of the formula VI and

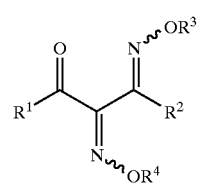

D) subsequent oximation of VI with hydroxylamine to give compounds of the formula I.

14 Claims, No Drawings

METHOD FOR THE PRODUCTION OF TRIOXIME DERIVATIVES

This application is a 371 of PCT/EP01/07660 filed Jul. 4, 2001.

The present invention relates to a process for preparing trisoxime derivatives of the formula I

I in which the substituents $R^1$ and $R^2$ can be identical or different and can in each case be cyano, $C_1$–$C_4$-alkyl, $C_1$–$C_4$-haloalkyl and $C_3$–$C_6$-cycloalkyl and $R^3$ and $R^4$ can be identical or different and can in each case be $C_1$–$C_4$-alkyl, $C_1$–$C_4$-haloalkyl, $C_3$–$C_6$-cycloalkyl, $C_1$–$C_4$-alkylcarbonyl and aryl-$C_1$–$C_4$-alkyl, by the following reaction steps in water without isolation of the intermediates:

A) nitrosation of 1,3-diketones of the formula II

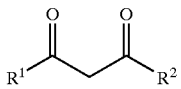

II to give monooximes of the formula III,

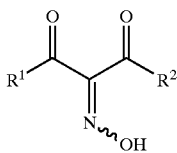

III

B) oximation of III with hydroxylamine derivatives of the formula IV

 IV in which $R^{3'}$ is hydrogen or a group $R^3$, or acid addition salts thereof, to give bisoximes of the formula V,

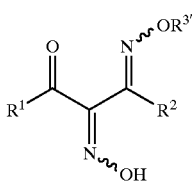

V

C) alkylation of V with alkylating agents or acylation of V with acylating agents to give compounds of the formula VI and

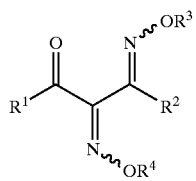

VI

D) subsequent oximation of VI with hydroxylamine to give compounds of the formula I.

The prior art discloses various methods for synthesizing oximes and O-alkyl oxime ethers [Houben-weyl, Methoden der organischen Chemie, (Methods of Organic Chemistry), 4th Ed., Vol. 10/4, pp. 17 ff., 55 ff., 73 ff., 217 ff., Thieme Verlag Stuttgart and New York (1979)].

Methods for alkylating activated oximes have also been disclosed in the prior art.

Gazz. Chim. Ital., Vol. 22, (1922), 289 ff. describes the synthesis of pentane 2,3,4-trisoxime and its benzylation to give the trisbenzyl oxime ether.

The synthesis of pentane 2,3,4-trisoxime from isonitrosoacetylacetone using hydroxylammonium chloride in water is disclosed in Rev. Acad. Cienc. Exactas, Fis.-Quim. Nat. Zaragoza, 31, (1976) 91–100.

Bull. Acad. Sci. USSR, Div. Chem. Sci. (Engl. Transl.), EN, 28, (1979), 121–128 describes alkylation reactions of oximes by diazoalkanes, alkyl halides and dialkyl sulfates; in particular, the competition between oxygen and nitrogen alkylation is studied. The preparation of the O-alkyl ethers of α,α'-bis-carbonyl oximes in acetone, ethanol, water or diethyl ether with moderate yields is described. To promote O-alkylation, it is recommended to operate at relatively high temperatures, since the nitrones are temperature-labile, or to use relatively large alkylating agents.

Ind. J. Chem., 30B, (1991), 749–753, describes the methylation of oximes of the formula III in which $R^1$ and $R^2$ are methyl or phenyl. The reaction with methyl iodide in the presence of anhydrous $K_2CO_3$ in acetone gives the O-methyl ethers in yields of 65 and 67%, respectively.

It is an object of the present invention to provide an economical and safe process, suitable for use on an industrial scale, for preparing O-alkyl or O-acyl oxime ethers of the formula I which provides access to the end products with high selectivity and yields and which does not require any change of solvent or isolation of intermediates.

We have found that this object is achieved by the process defined at the outset.

The process according to the invention achieved the object since all synthesis steps are carried out in the solvent water, without separation, isolation or purification of intermediates being required. It is also possible to add to the water small amounts (up to 50% by volume, in particular up to 10% by volume) of inert water-miscible organic solvents to promote the course of the reaction in the case of poorly soluble starting materials, intermediates or end products.

In a preferred embodiment of the process according to the invention, no organic solvent is added.

The reactions of steps A to D are known per se from the literature; they are usually carried out in organic solvents, such as aromatic hydrocarbons, ethers or alcohols. However, it has not been known that bis- and trisoximes and the corresponding oxime ethers can be prepared by this route in the solvent water with such a high selectivity that an isolation of the intermediates is not required.

In the first step (step A) of the process, 1,3-diketones of the formula II are nitrosated. The nitrosation is carried out under acidic conditions using $C_1$–$C_4$-alkyl nitrites (cf. Chem. Ber., 20, (1887), 252 and 656) or alkali metal or alkaline earth metal nitrites (cf. J. Chem. Soc., (1957), 3052), or else using nitrogen oxide (NO) and atmospheric oxygen (cf. Chem. Ber., 37, (1904) 1524). Preference is given to using alkali metal or alkaline earth metal nitrites, in particular potassium nitrite or sodium nitrite, at a pH 3 5. The type of acid is usually immaterial; for practical reasons, the pH is adjusted by adding inorganic acids, such as hydrochloric or sulfuric acid.

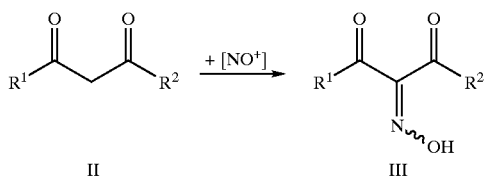

This reaction is usually carried out at from –10° C. to +120° C., preferably from 0° C. to 80° C., in the presence of an acid.

The starting materials are generally reacted with one another in equimolar amounts. In terms of yield, it may be advantageous to employ an excess of the nitrite, based on II.

1,3-Diketones of the formula II are commercially available.

In the second step (step B), the monooximes of the formula III are reacted with hydroxylamine derivatives of the formula IV to give bisoximes of the formula V.

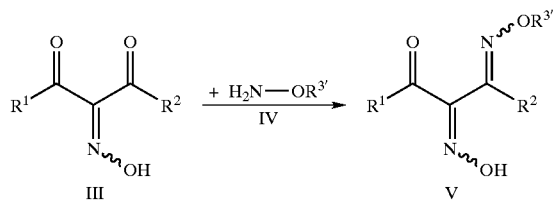

In the formula IV, $R^{3'}$ is hydrogen or a group $R^3$. In one embodiment of the process, using hydroxylamine ethers in which $R^{3'}$ is $R^3$, the reaction can directly give the bisoxime monoethers V.

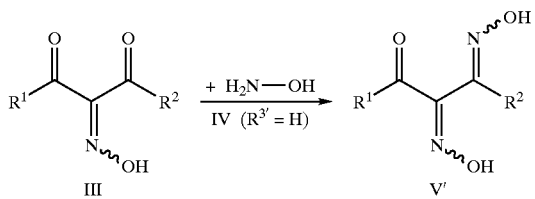

In another embodiment of the process, the monooxime is reacted with hydroxylamine of the formula IV ($R^{3'}$=H) to give bisoximes V', and the two oxime groups are alkylated or acylated only in the next step C). This embodiment only gives compounds in which $R^3$ and $R^4$ are identical.

In both embodiments, the reaction is independent of the pH. For practical reasons, the reaction is usually carried out under the same or similar pH conditions as the first step.

In both embodiments, the hydroxylamine derivatives of the formula IV can be employed either as free bases or as acid addition salts. For practical reasons, the corresponding hydrochlorides or hydrosulfates are frequently used.

The reaction of III with IV is usually carried out at from –10° C. to 120° C., preferably from 0° C. to +120° C.

In the third step (step C), the bisoxime monoethers V or the bisoximes V' are converted, using alkylating or acylating agents, into the bisoxime diethers VI.

Suitable alkylating agents are $C_1$–$C_4$-alkyl halides, $C_1$–$C_4$-haloalkyl halides, $C_3$–$C_6$-cycloalkyl halides, $C_1$–$C_4$-alkylcarbonyl halides and aryl-$C_1$–$C_4$-alkyl halides, or else the corresponding sulfonates or p-toluene sulfonates or dialkyl carbonates, dialkyl sulfates, in particular dimethyl sulfate. From the group of the halides, preference is given to the bromides and chlorides.

Suitable acylating agents are the halides, in particular chlorides, of $C_1$–$C_4$-alkylcarboxylic acids, or corresponding anhydrides. Preference is given to using acetyl chloride and acetic anhydride.

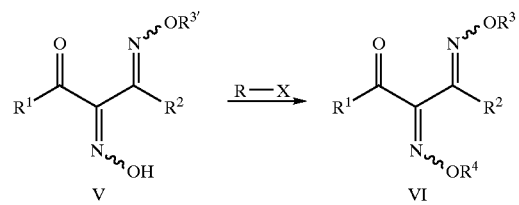

In the reaction scheme above "R" is a group $R^3$ and/or $R^4$ of the meaning $C_1$–$C_4$-alkylcarbonyl and "X" is a leaving group, such as halogen or alkylcarbonyloxy.

This reaction is usually carried out at from –10° C. to +120° C., preferably from 0° C. to 70° C., in the presence of a base, so that the oxime groups are at least partially deprotonated. The reaction is advantageously carried out at a pH of 7–14, in particular at a pH of 10–14.

The process according to the invention is not limited to certain substituted compounds, provided the substituents are inert under the reaction conditions. Aliphatic radicals can be straight-chain or branched. The chain length of the substituents is immaterial for the process according to the invention; however, for technical reasons, radicals having a maximum of 4 carbons will usually be chosen.

Very particularly preferably, the process is used for preparing pentane-2,3,4-trione-3,4-O-methyl oxime.

The substituents $R^1$ and $R^2$ may carry further radicals which are inert under the reaction conditions, for example: halogen, cyano, $SO_3H$, COOH, $COOR^b$, alkyl, alkenyl, alkynyl, aryl or heteroaryl; $R^b$ is $C_1$–$C_{10}$-alkyl.

Alkyl is generally $C_1$–$C_{10}$-alkyl, in particular $C_1$–$C_4$-alkyl, this also applies to haloalkyl; cycloalkyl radicals have 3 to 6 ring members. Aryl is, for example, phenyl or naphthyl.

Heteroaryl is, for example, furyl, thienyl, pyrrolyl, isoxazolyl, isothiazolyl, pyrazolyl, oxazolyl, imidazolyl, pyridyl, pyridazinyl, pyrimidinyl or triazinyl.

Halogens is chlorine, fluorine, bromine or iodine.

Alkenyl and alkynyl radicals have two to eight, in particular three to six carbon atoms.

The O-alkyl oxime ethers obtainable by the process according to the invention are suitable for use as intermediates in the preparation of dyes or active compounds in the pharmaceutical or crop protection sector.

The examples below are meant to illustrate the process according to the invention in more detail:

EXAMPLES

Step A): Synthesis of acetylhydroxyiminoacetone

A solution of 69.0 g (1 mol) of $NaNO_2$ in 103 g water was adjusted to pH 4.0–4.6 using 50% by weight strength $H_2SO_4$. At about 15° C., a mixture of 100.0 g (1 mole) of acetylacetone and 475 g of water was metered in at constant pH over a period of 105 min. During the reaction, a product-containing organic phase was formed.

According to gas chromatographic analysis, the conversion of acetyl acetone was quantitative.

The reaction solution was used for the next step without any purification.

Step B): Synthesis of pentane-2,3,4-trione (3-O-methyl oxime) 4-oxime

The reaction solution of step 1 was, at about 20 to 25° C., admixed with 306.0 g of a 30% by weight strength aqueous solution of methoxyamine hydrochloride, over a period of about 2 hours. By adding 25% by weight strength NaOH solution, the pH was maintained at 4.0–4.6. After 3 hours, the oily product-containing phase was analyzed by gas chromatography. In the gas chromatogram, the various isomers of the title compound accounted for about 83 area %.

The reaction solution was used for the next step without any purification.

Step C): Methylation to give pentane-2,3,4-trione 3,4-bis(O-methyl oxime)

The reaction solution of step 2 was adjusted to pH 10–11 using 25% by weight strength NaOH solution. At this pH, 138.7 g (1.1 mol) of dimethyl sulfate were added at about 20–25° C. over a period of about 90 min., and the solution was stirred for a further 90 min.

The reaction solution was used for the next step without any purification.

Step D): Synthesis of pentane-2,3,4-trione 3,4-bis (O-methyl oxime) 2-oxime

The reaction solution of step 3 was adjusted to pH 13–14 using 25% by weight strength NaOH solution and then, at about 20–25° C. and at constant pH, admixed with 106.7 g (1.1 mol) of a 30% by weight strength aqueous solution of hydroxylammonium sulfate, over a period of about 60–75 min. After a further hour of stirring, the solution was acidified slightly (to pH 6) and the reaction solution was extracted with methyl tert-butyl ether (MTBE). The organic phase was washed with water and dried, and the solvent was then removed.

This gave 177 g of the title compound.

According to HPLC analysis, the yield, based on the acetyl acetone employed, was 62–63% of theory. According to HPLC analysis using an internal standard, the crude product contained the following isomers (% by weight)

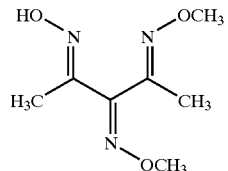

E, Z, E isomer
17.5%

-continued

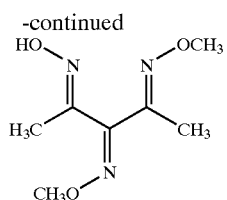

E, E, E isomer
35.0%

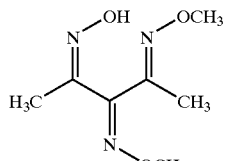

E, Z, Z isomer
11.9%

We claim:
1. A process for preparing trioxime derivatives of the formula I

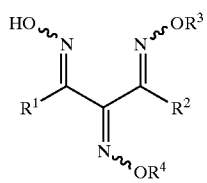

in which the substituents $R^1$ and $R^2$ are identical or different and each is cyano, $C_1$–$C_4$-alkyl, $C_1$–$C_4$-haloalkyl or $C_3$–$C_6$-cycloalkyl, and $R^3$ and $R^4$ are identical or different and each is $C_1$–$C_4$-alkyl, $C_1$–$C_4$-haloalkyl, $C_3$–$C_6$-cycloalkyl, $C_1$–$C_4$-alkylcarbonyl or aryl-$C_1$–$C_4$-alkyl, by the following reaction steps in water without isolation of the intermediates:

A) nitrosation of 1,3-diketones of the formula II

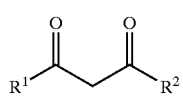

to give monooximes of the formula III,

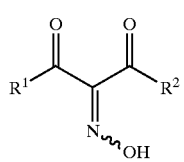

B) oximation of III with hydroxylamine derivatives of the formula IV

$H_2N$—$OR^{3'}$ in which $R^{3'}$ is hydrogen or a group $R^3$, or acid addition salts thereof, to give bisoximes of the formula V,

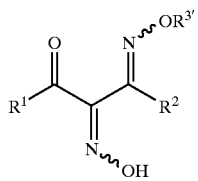

V

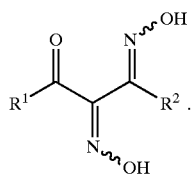

V'

C) alkylation of V with alkylating agents or acylation of V with acylating agents to give compounds of the formula VI and

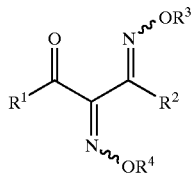

VI

D) subsequent oximation of VI with hydroxylamine to give compounds of the formula I.

2. A process as claimed in claim 1 where the nitrosation in step A is carried out under acidic conditions using an alkali metal nitride or alkaline earth metal nitride.

3. A process as claimed in claim 1 where the substituents $R^3$ and $R^4$ in formula I are identical.

4. A process as claimed in claim 3 where in step B $R^{3'}$ in formula IV is not hydrogen.

5. A process as claimed in claim 3 where in step B the compound of the formula III is reacted with hydroxylamine to give bisoximes of the formula V'

6. A process as claimed in claim 1 where the substituents $R^3$ and $R^4$ in formula I are different.

7. A process as claimed in claim 1 where $R^{3'}$ in formula IV is $C_1$–$C_4$-alkyl, $C_1$–$C_4$-haloalkyl or aryl-$C_1$–$C_4$-alkyl.

8. A process as claimed in claim 1 where alkylating agents are used in step C.

9. A process as claimed in claim 1 where acylating agents are used in step C.

10. A process as claimed in claim 1 where the substituents $R^1$, $R^2$, $R^3$ and $R^4$ in formula I are $C_1$–$C_4$-alkyl.

11. A process as claimed in claim 2 wherein the alkali metal nitride is potassium nitride or sodium nitride.

12. A process as claimed in claim 8 wherein the alkylating agents are dialkyl sulfates.

13. A process as claimed in claim 12 wherein the dialkyl sulfate is dimethyl sulfate.

14. A process as claimed in claim 9 wherein the acylating agents are $C_1$–$C_4$-carbonyl halides or $C_1$–$C_4$-carboxylic anhydrides.

* * * * *